United States Patent [19]

Glaser

[11] Patent Number: Plant 5,913

[45] Date of Patent: Mar. 24, 1987

[54] AZALEA PLANT NAMED LUCI

[76] Inventor: Karl Glaser, Stadtteil Harreshausen, Ausserhalb 25, 6113 Babenhausen 5, Fed. Rep. of Germany

[21] Appl. No.: 699,457

[22] Filed: Feb. 7, 1985

[51] Int. Cl.[4] ..... A01H 5/00

[52] U.S. Cl. ..... Plt./56

[58] Field of Search ..... Plt./56–57

*Primary Examiner*—Robert E. Bagwill

*Attorney, Agent, or Firm*—Schwartz, Jeffery, Schwaab, Mack, Blumenthal & Evans

[57] ABSTRACT

An azalea plant named Luci characterized by its intense bright pink flower color, very large flowers which are double in form, excellent growth habit, ease of propagation, early response, and its ability to grow and blossom at relatively low temperatures.

2 Drawing Figures

The present invention comprises a new and distinct cultivar of Rhododendron L, commonly referred to as azalea, and known by the cultivar name Luci.

Luci is the product of a planned breeding program which has the general objective of creating new azalea cultivars having early response and having the capability of developing and blossoming at relatively low temperatures, for example, temperatures as low as in the range of 5°–6° C. The development of a cultivar having relatively intense pink flower color, in addition to the above noted characteristics, was also an objective of the breeding program. Such characteristics in combination were not present or were in need of improvement in previously available commercial cultivars.

Luci was originated from a cross made in a controlled breeding program in Babenhausen, Federal Republic of Germany. The male and female parents of the cross are not specifically identifiable at this time, although it is the recollection of applicant that the cultivar named Dr. Arnold was one of such parents. The original cross was made in 1972, and in 1974 the progeny of the cross blossomed for the first time. Luci was selected from such progeny, and the first act of asexual reproduction of Luci was accomplished when vegetative cuttings were taken in 1974 by applicant in a controlled greenhouse environment in Babenhausen, Federal Republic of Germany. Subsequent examination demonstrated that the combination of characteristics as herein disclosed for Luci are firmly fixed and are retained through successive generations of asexual reproduction.

Luci has not been observed under all possible environmental conditions. The phenotype may vary significantly with variations in environment such as temperature, light intensity, and day length, and may also vary through the application of growth regulators. The following descripton is based on plants of the new cultivar grown in Babenhausen, Federal Republic of Germany under greenhouse conditions which approximate those generally used in commercial practice.

The following traits have been repeatedly observed and are determined to be basic characteristics of Luci, which in combination distinguish this azalea as a new and distinct cultivar:

(1) Intense, bright pink flower color, and a floriferous flowering habit.

(2) Blossoms are double in form, and very large, reaching a diameter of up to 12 cm. The size of the blossoms depends on when the plant is pinched, how the plants are nourished, and the growing conditions, e.g. light intensity and day length. Growth regulators such as alar can reduce blossom size by up to one third.

(3) Easy to propagate, with the roots of the cuttings developing quickly.

(4) With proper pinching, a symetrical and relatively large, yet compact, plant is developed.

(5) Excellent growth habit, even during the low light and low temperature conditions of winter greenhouse cultivation.

(6) Early response, with plants having buds showing color and ready to be sold in as little as approximately 130 days after pinching, during high light periods. Low light and temperature conditions, and the use of growth regulators, e.g. alar, can delay flowering several weeks.

(7) The early response is not significantly affected by low temperatures. Although temperatures such as 5°–6° C. slow the development and response to some extent, the low temperature response of Luci is excellent compared to existing varieties. From an energy standpoint, this is a significant characteristic.

(8) Color intensity is strongest during August to October. With shorter days, the color is somewhat faded. The blossoms retain their color for approximately 14 days before fading, but remain attractive for 3–6 weeks.

The accompanying photographic drawings show typical inflorescence and foliage characteristics of Luci, with the colors being as nearly true as possible with illustrations of this type.

Sheet 1 is a color photograph of Luci, in top perspective view in pot form.

Sheet 2 is a color photograph showing enlarged a typical blossom of Luci, in plan view.

It should be noted that the color depicted in the color photographs does not precisely show the true flower color, although the color values are accurately set forth below. In Sheet 1, the intensity of the pink flower color does not appear, although the color is generally correct. The enlarged flower shown in Sheet 2 is more red than the actual flower color, and this photograph is primarily of value in showing flower form.

In the following description, color references are made to The Royal Horticultural Society Colour Chart, and were taken in Babenhausen, Federal Republic of Germany.

Classification:

*Botanical.*—Rhododendron L, cv Luci.

*Commercial.*—Pot azalea.

PLANT

Growth habit: Good to excellent, developing rapidly and symetrically with adequate pinching. Requires pinching earlier and more often than other azalea cutivars of this general type, with 3–5 pinches producing a symetrical and relatively large plant. The cultivar is particularly resistant to low temperatures, growing well even during winter conditions of low light and low temperatures in the range of 5°–6° C.

Branching: Satisfactory to very good. After the first pinching, young shoots begin to grow quite rapidly early, and in large quantities, particularly after additional pinchings.

Response period: The response period is very short for this type of cultivar. The response varies considerably depending upon light and temperature conditions, and the application of growth regulators. For plants pinched in mid-May for the first time, plants having buds showing color and ready to be sold are available approximately 130–135 days later. Where growth is under less light and lower temperature conditions, the response period may be up to 130–150 days, and the application of alar for growth regulation can delay the response period for up to 7–8 weeks.

Ease of propagation: Good to very good. Cuttings root quickly and firmly.

Buds: Generally elliptical in shape. Plant may be cultivated without break and blossoms regularly. A particular advantage of the cultivar is that bud development proceeds in low temperature conditions, for example, at approximately 5° C. This low temperature development is not common to most azalea varieties of this type. But development is faster at higher temperatures.

Leaves: Young shoots are green in color, changing to a mid-green in young and fully grown leaves; color under surface of young leaves is light green, and mid-green on fully grown leaves. Fully grown leaves are slightly convex, and generally oval in shape, terminating in a blunt point. The fully grown leaves are slightly shiny on the top surface, and the overall length and width of the fully grown leaves are generally average for this type of azalea.

BLOSSOM

Shape and size: The blossoms have the shape of a wide horn, and are double and very large, reaching a diameter of up to 12 cm. The diameter of the blossoms depends on the extent of pinching, growing conditions, and nourishment. Generally speaking, late pinching and low light conditions will result in blossoms having a relatively smaller diameter. The blossoms tend to reach their greatest diameter during periods of high light and long day length. The diameter of the blossoms are adversely affected by growth regulation, such as treatments with alar, which treatment is recommended only for small plants. The blossoms are carried on relatively long stems, 1.0 to 1.5 cm., and in view of the size and form of the blossom, there is a tendency for the blossom to hang or bend somewhat on the stem. This characteristic can be controlled by pinching.

Color: The color is an intense and bright pink 57C, with barely perceptible red spots appearing irregularly on the petals. The red dots are 53C in color, and appear mainly where plants are treated with alar. The throat of the blossom is a somewhat brighter pink than 57C.

Temperature tolerance: The development and maturing of the blossoms is not significantly impeded at relatively low temperatures, an important characteristic of the cultivar, although optimum temperatures for blossoming is in the range of 12°–18° C., having regard to energy costs and optimum blossom characteristics. For example, during the period from November to January, the time for developing blossoms from buds showing color was approximately 16 days at approximately 15° C.

Normal blossoming period: From the end of August to mid-November, although year around flowering is achieved by greenhouse cultivation.

Blossom life: Blossoms hold their intense pink flower color for approximately 14 days, after which the blossoms begin to fade in color. The intensity and luminosity of the pink color is strongest from August to October, and as the days get shorter, the pink blossom color is somewhat less intense. The blossoms remain attractive for approximately 3–6 weeks, depending upon geographical location and season.

Corona: Relatively long, 5 in number, with the tip of the corona being relatively wide.

Reproductive organs: The reproductive organs of Luci are not distinctive.

I claim:

1. A new and distinct cultivar of azalea plant named Luci, as described and illustrated, and particularly characterized by its intense bright pink flower color, very large flowers which are double in form, excellent growth habit, ease of propagation, early response, and its ability to grow and blossom at relatively low temperatures.

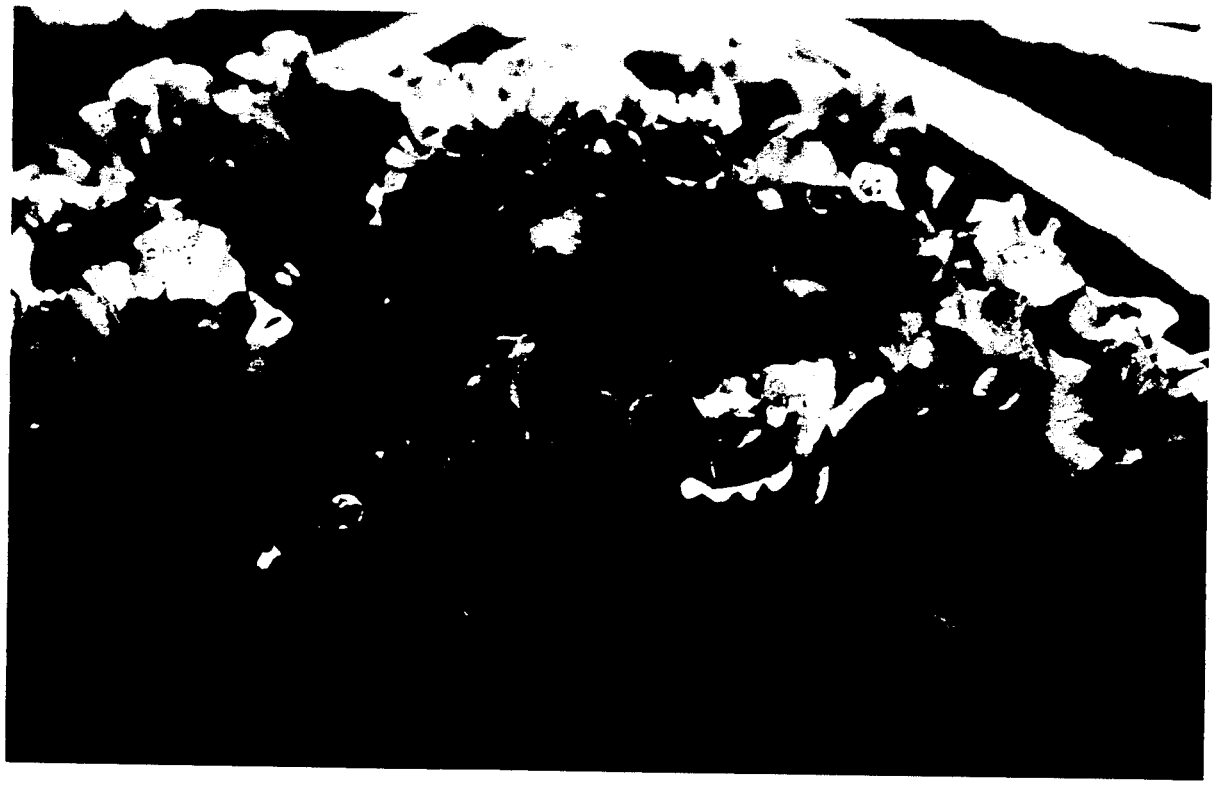

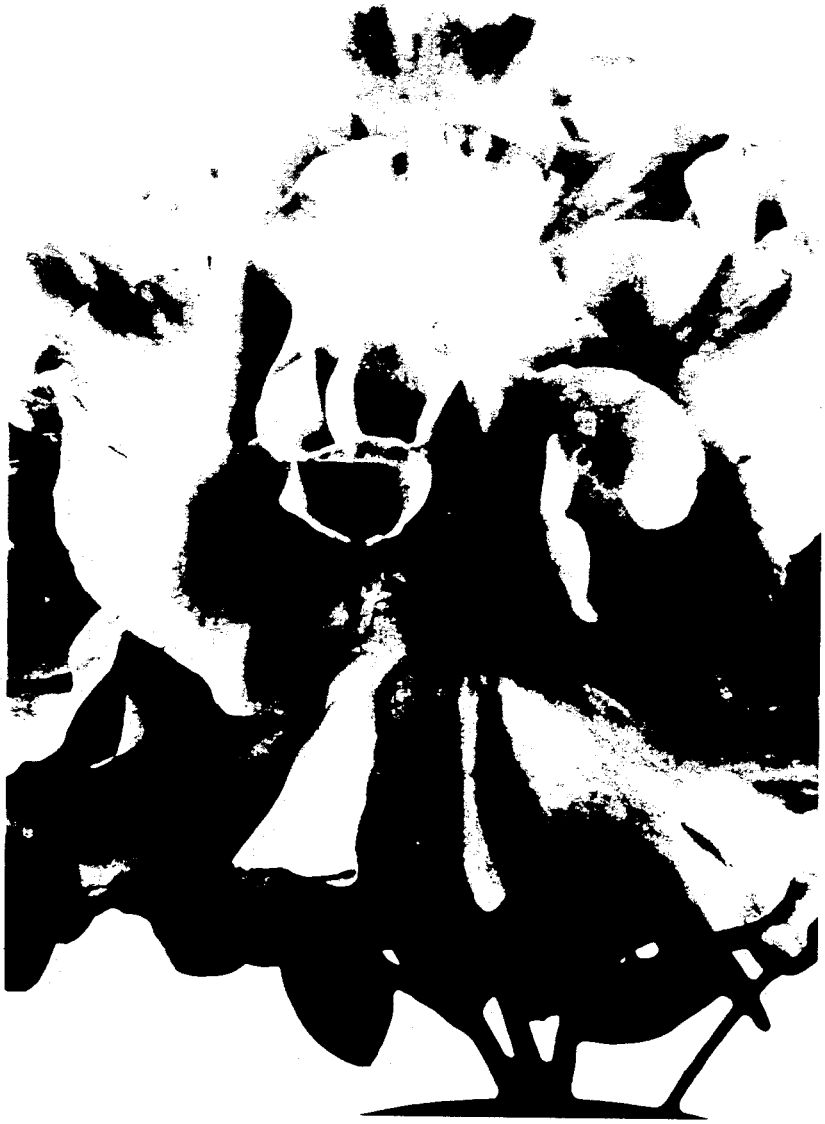

* * * * *